United States Patent
Bacon

(10) Patent No.: US 7,721,731 B2
(45) Date of Patent: May 25, 2010

(54) DISPENSER

(75) Inventor: Raymond John Bacon, Petersfield (GB)

(73) Assignee: Clinical Designs Ltd., Hampshire (GB)

( * ) Notice: Subject to any disclaimer, the term of this patent is extended or adjusted under 35 U.S.C. 154(b) by 812 days.

(21) Appl. No.: 10/545,848

(22) PCT Filed: Feb. 20, 2004

(86) PCT No.: PCT/GB2004/000706

§ 371 (c)(1),
(2), (4) Date: Jul. 10, 2006

(87) PCT Pub. No.: WO2004/073776

PCT Pub. Date: Sep. 2, 2004

(65) Prior Publication Data

US 2007/0062522 A1 Mar. 22, 2007

(30) Foreign Application Priority Data

Feb. 21, 2003 (GB) ................. 0304000.3

(51) Int. Cl.
*A61M 11/00* (2006.01)
*B05D 7/14* (2006.01)

(52) U.S. Cl. ..................... 128/200.23; 128/200.14; 128/200.17; 128/203.12; 128/203.13; 128/203.14; 128/203.15; 222/402.1; 222/494; 222/528; 239/337

(58) Field of Classification Search ............ 128/200.14, 128/200.17, 200.23, 203.12, 203.15, 203.21–203.23; 222/402.1, 494, 528; 239/337
See application file for complete search history.

(56) References Cited

U.S. PATENT DOCUMENTS

| 2,002,835 A | 5/1935 | Rose |
| 2,716,013 A | 8/1955 | Tinker |
| 2,773,631 A | 12/1956 | Bryant |
| 2,922,613 A | 1/1960 | Beacham et al. |
| 2,974,835 A | 3/1961 | Herbrick |
| 3,012,454 A | 12/1961 | Brodbeck |
| 3,103,335 A | 9/1963 | Martinez |
| 3,181,743 A | 5/1965 | Libit et al. |
| 3,187,748 A | 6/1965 | Mitchell et al. |
| 3,190,497 A | 6/1965 | Anthon |
| 3,294,293 A | 12/1966 | Johns |
| 3,305,144 A | 2/1967 | Beres et al. |
| 3,329,389 A | 7/1967 | Clark |

(Continued)

FOREIGN PATENT DOCUMENTS

AU 776816 7/2002

(Continued)

*Primary Examiner*—Steven O Douglas
*Assistant Examiner*—Valerie Skorupa
(74) *Attorney, Agent, or Firm*—Alfred A. Fressola; Ware, Fressola, Van Der Sluys & Adolphson LLP

(57) ABSTRACT

An inhalant dispenser has a cover 3 pivotally carried on a body 6. The cover has a cam arrangement for lifting a junction member 41 against the action of the spring in an inhalant can C. Lifting of the junction member cocks a breath actuated dose release mechanism. The latter includes a flap 61 in the breath path. The flap is carried on the junction member and is arranged to release a hinged member 48 by action of latches 70 on the flap and sears on the hinged member.

18 Claims, 8 Drawing Sheets

U.S. PATENT DOCUMENTS

| | | | |
|---|---|---|---|
| 3,395,838 A | 8/1968 | Beres et al. | |
| 3,439,846 A | 4/1969 | Evras | |
| 3,456,646 A | 7/1969 | Phillips et al. | |
| 3,789,843 A | 2/1974 | Armstrong et al. | |
| 3,789,943 A | 2/1974 | Kampert et al. | |
| 3,913,882 A | 10/1975 | Moulet | |
| 3,926,339 A | 12/1975 | Openchowski | |
| 3,926,347 A | 12/1975 | Low et al. | |
| 4,085,886 A | 4/1978 | Nishioka | |
| 4,109,836 A | 8/1978 | Falarde | |
| 4,142,651 A | 3/1979 | Leopoldi et al. | |
| 4,354,660 A | 10/1982 | Stupar et al. | |
| 4,414,972 A | 11/1983 | Young et al. | |
| 4,457,699 A | 7/1984 | Hattori | |
| 4,570,898 A | 2/1986 | Staeubli | |
| 4,576,157 A | 3/1986 | Raghuprasad | |
| 4,664,107 A * | 5/1987 | Wass | 128/200.23 |
| 4,703,761 A | 11/1987 | Rathbone et al. | |
| 4,707,038 A | 11/1987 | Voegeli | |
| 4,803,978 A | 2/1989 | Johnson, IV et al. | |
| 4,817,822 A | 4/1989 | Rand et al. | |
| 4,819,834 A | 4/1989 | Thiel | |
| 4,863,379 A | 9/1989 | Timerdahl et al. | |
| 4,955,371 A | 9/1990 | Zamba et al. | |
| 4,972,830 A | 11/1990 | Wong et al. | |
| 5,020,527 A | 6/1991 | Dessertine | |
| 5,031,610 A | 7/1991 | Armstrong et al. | |
| 5,042,526 A | 8/1991 | Kulakoff | |
| 5,060,643 A | 10/1991 | Rich et al. | |
| 5,069,204 A | 12/1991 | Smith et al. | |
| 5,113,855 A | 5/1992 | Newhouse | |
| 5,119,806 A | 6/1992 | Palson et al. | |
| 5,152,456 A | 10/1992 | Ross et al. | |
| 5,184,761 A | 2/1993 | Lee | |
| 5,193,745 A | 3/1993 | Holm | |
| 5,217,004 A | 6/1993 | Blasnik et al. | |
| 5,224,472 A | 7/1993 | Pesenti et al. | |
| 5,239,992 A | 8/1993 | Bougamont et al. | |
| 5,273,172 A | 12/1993 | Rossbach et al. | |
| 5,295,479 A | 3/1994 | Lankinen | |
| 5,297,542 A | 3/1994 | Bacon | |
| 5,347,998 A | 9/1994 | Hodson et al. | |
| 5,370,279 A | 12/1994 | Tardif | |
| 5,388,572 A | 2/1995 | Mulhauser et al. | |
| 5,402,823 A | 4/1995 | Cole | |
| 5,408,994 A | 4/1995 | Wass et al. | |
| 5,421,482 A | 6/1995 | Garby et al. | |
| 5,447,150 A | 9/1995 | Bacon | |
| 5,469,843 A | 11/1995 | Hodson | |
| 5,487,378 A | 1/1996 | Robertson et al. | |
| 5,501,375 A | 3/1996 | Nilson | |
| 5,511,540 A | 4/1996 | Bryant et al. | |
| 5,546,932 A | 8/1996 | Galli | |
| 5,549,101 A | 8/1996 | Trofast et al. | |
| 5,549,226 A | 8/1996 | Kopp | |
| 5,611,444 A | 3/1997 | Garby et al. | |
| 5,623,920 A | 4/1997 | Bryant | |
| 5,645,050 A | 7/1997 | Zierenberg et al. | |
| 5,655,523 A | 8/1997 | Hodson et al. | |
| 5,667,142 A | 9/1997 | Newman | |
| 5,692,492 A | 12/1997 | Bruna et al. | |
| 5,707,038 A | 1/1998 | Cocatre-Zilgien | |
| 5,740,793 A | 4/1998 | Hodson et al. | |
| 5,772,085 A | 6/1998 | Bryant et al. | |
| 5,996,577 A | 12/1999 | Ohki et al. | |
| 6,085,742 A | 7/2000 | Wachter et al. | |
| 6,149,054 A | 11/2000 | Cirrillo et al. | |
| 6,205,999 B1 | 3/2001 | Ivri et al. | |
| 6,234,168 B1 | 5/2001 | Bruna | |
| 6,240,918 B1 | 6/2001 | Ambrosio et al. | |
| 6,260,549 B1 | 7/2001 | Sosiak | |
| 6,283,365 B1 | 9/2001 | Bason | |
| 6,354,290 B1 | 3/2002 | Howlett | |
| 6,397,839 B1 | 6/2002 | Stradella | |
| 6,405,727 B1 | 6/2002 | MacMichael et al. | |
| 6,415,784 B1 | 7/2002 | Christrup et al. | |
| 6,422,234 B1 * | 7/2002 | Bacon | 128/200.14 |
| 6,427,683 B1 | 8/2002 | Drachmann et al. | |
| 6,431,168 B1 | 8/2002 | Rand et al. | |
| 6,439,227 B1 | 8/2002 | Myrman et al. | |
| 6,442,234 B1 | 8/2002 | Morken et al. | |
| 6,443,146 B1 | 9/2002 | Voges | |
| 6,460,537 B1 | 10/2002 | Bryant et al. | |
| 6,510,847 B1 | 1/2003 | Helgesson et al. | |
| 6,553,988 B1 | 4/2003 | Holroyd | |
| 6,581,590 B1 | 6/2003 | Genova et al. | |
| 6,601,582 B2 | 8/2003 | Rand et al. | |
| 6,615,827 B2 | 9/2003 | Greenwood et al. | |
| 6,637,432 B2 | 10/2003 | Wakefield et al. | |
| 6,655,379 B2 | 12/2003 | Clark et al. | |
| 6,659,307 B1 | 12/2003 | Stradella | |
| 6,755,190 B2 | 6/2004 | Rasmussen | |
| 6,866,037 B1 | 3/2005 | Aslin et al. | |
| 6,866,038 B2 * | 3/2005 | Bacon | 128/200.23 |
| 6,907,876 B1 | 6/2005 | Clark et al. | |
| 6,926,002 B2 | 8/2005 | Scarrott et al. | |
| 7,036,505 B2 * | 5/2006 | Bacon et al. | 128/203.13 |
| 7,047,964 B2 * | 5/2006 | Bacon | 128/200.23 |
| 7,093,594 B2 | 8/2006 | Harrison et al. | |
| 7,107,986 B2 | 9/2006 | Rand et al. | |
| 7,225,805 B2 * | 6/2007 | Bacon | 128/200.23 |
| 7,341,057 B2 | 3/2008 | Scarrott et al. | |
| 7,387,121 B2 | 6/2008 | Harvey | |
| 7,454,267 B2 | 11/2008 | Bonney et al. | |
| 7,597,099 B2 | 10/2009 | Jones et al. | |
| 2001/0013343 A1 | 8/2001 | Andersson | |
| 2002/0056449 A1 | 5/2002 | Wakefield et al. | |
| 2003/0089368 A1 | 5/2003 | Zhao | |
| 2003/0136401 A1 | 7/2003 | Jansen et al. | |
| 2004/0025868 A1 | 2/2004 | Bruna | |
| 2004/0089299 A1 | 5/2004 | Bonney et al. | |
| 2004/0134488 A1 | 7/2004 | Davies | |
| 2004/0144798 A1 | 7/2004 | Ouyang et al. | |
| 2005/0205512 A1 | 9/2005 | Scarrott et al. | |
| 2006/0231093 A1 | 10/2006 | Burge et al. | |
| 2006/0278225 A1 | 12/2006 | MacMichael et al. | |
| 2007/0062518 A1 | 3/2007 | Geser et al. | |
| 2007/0089735 A1 | 4/2007 | Langfor et al. | |
| 2008/0066750 A1 | 3/2008 | Minshull et al. | |

FOREIGN PATENT DOCUMENTS

| | | |
|---|---|---|
| DE | 629163 | 4/1936 |
| DE | 3324699 | 12/1984 |
| DE | 8715223 | 2/1988 |
| DE | 3734894 | 3/1992 |
| DE | 4111895 | 10/1992 |
| DE | 19745513 | 4/1999 |
| DE | 29818662 | 3/2000 |
| DE | 10061723 | 7/2002 |
| EP | 0312073 | 4/1989 |
| EP | 0414536 | 2/1991 |
| EP | 0428380 | 5/1991 |
| EP | 0501365 | 9/1992 |
| EP | 0629563 | 12/1994 |
| EP | 0764312 | 4/1998 |
| EP | 1104318 | 8/1999 |
| EP | 1003583 | 5/2000 |
| EP | 1019125 | 7/2000 |
| EP | 0883415 | 5/2002 |
| EP | 1229953 | 8/2002 |
| EP | 1254678 | 11/2002 |
| EP | 1267970 | 1/2003 |
| EP | 1267975 | 1/2003 |

| | | |
|---|---|---|
| FR | 2004766 | 5/1974 |
| FR | 2471535 | 6/1981 |
| FR | 2483262 | 12/1981 |
| FR | 2654627 | 5/1991 |
| FR | 2660630 | 10/1991 |
| FR | 2701653 | 8/1994 |
| GB | 161969 | 7/1922 |
| GB | 727195 | 3/1955 |
| GB | 939324 | 10/1963 |
| GB | 997617 | 7/1965 |
| GB | 1012565 | 12/1965 |
| GB | 1269811 | 4/1972 |
| GB | 1403826 | 8/1975 |
| GB | 2079183 | 1/1982 |
| GB | 2191032 | 12/1987 |
| GB | 2233236 | 1/1991 |
| GB | 2262452 | 6/1993 |
| GB | 2263873 | 8/1993 |
| GB | 2264238 | 8/1993 |
| GB | 2266466 | 11/1993 |
| GB | 2279571 | 1/1995 |
| GB | 2279879 | 1/1995 |
| GB | 2292891 | 3/1996 |
| GB | 2381461 * | 7/2003 |
| HU | 67279 | 3/1995 |
| JP | 63251880 | 10/1988 |
| JP | 06027550 | 4/1994 |
| WO | WO 92/07599 | 5/1992 |
| WO | WO 92/07600 | 5/1992 |
| WO | WO 92/09323 | 6/1992 |
| WO | WO 92/10229 | 6/1992 |
| WO | WO 93/03783 | 3/1993 |
| WO | WO 93/24167 | 12/1993 |
| WO | WO 94/05359 | 3/1994 |
| WO | WO 94/19042 | 9/1994 |
| WO | WO 95/08484 | 3/1995 |
| WO | WO 96/39337 | 12/1996 |
| WO | WO 98/41254 | 9/1998 |
| WO | WO 98/52634 | 11/1998 |
| WO | WO 99/36116 | 7/1999 |
| WO | WO 00/01436 | 1/2000 |
| WO | WO 01/32247 | 5/2001 |
| WO | WO 02/11802 | 2/2002 |
| WO | WO 02/38207 | 5/2002 |
| WO | WO 02/43794 | 6/2002 |
| WO | WO 02/053295 | 7/2002 |
| WO | WO 02/058772 | 8/2002 |
| WO | WO 03/010154 | 2/2003 |
| WO | WO 2003/012565 | 2/2003 |
| WO | WO 03/086518 | 10/2003 |
| WO | WO 2004/022142 | 3/2004 |
| WO | WO 2004/022143 | 3/2004 |
| WO | WO 2004/022242 | 3/2004 |

* cited by examiner

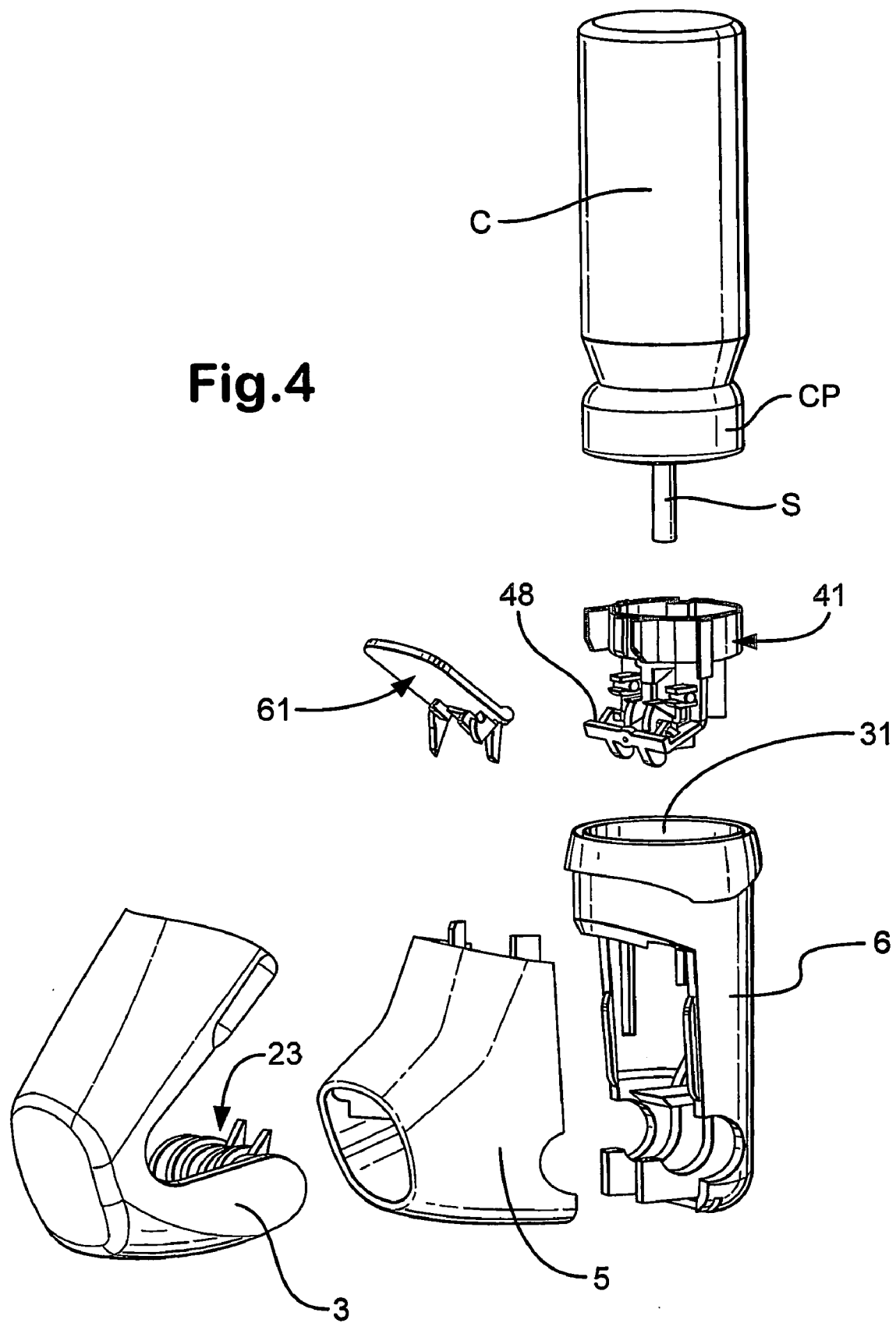

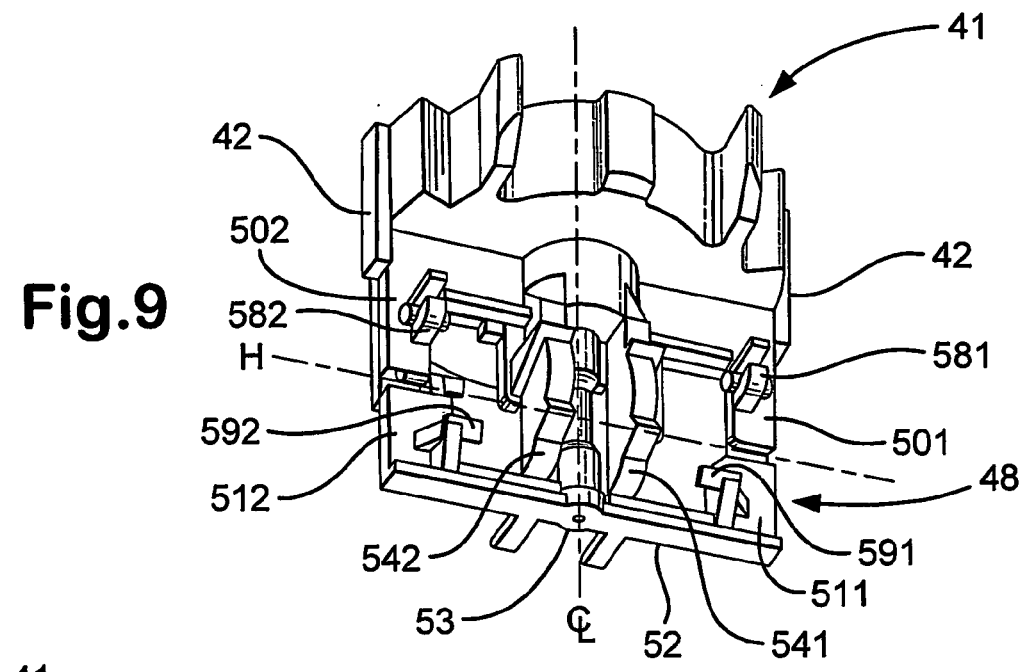
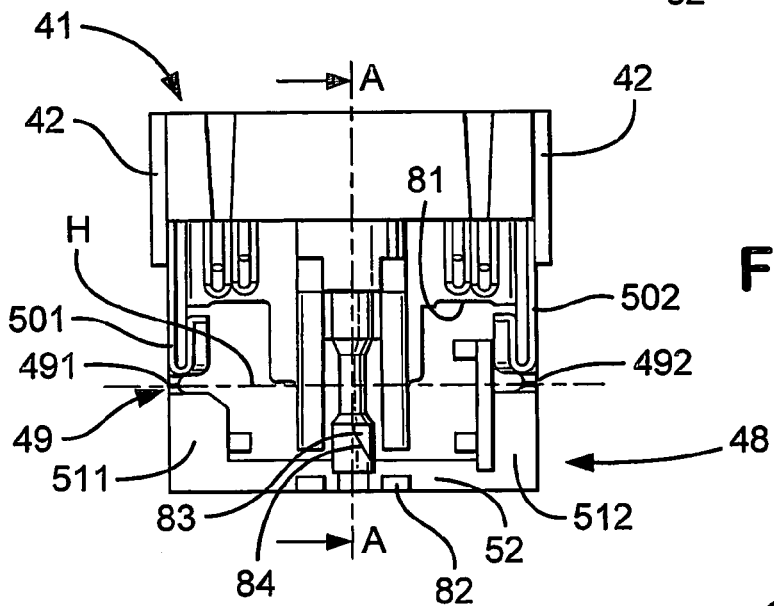
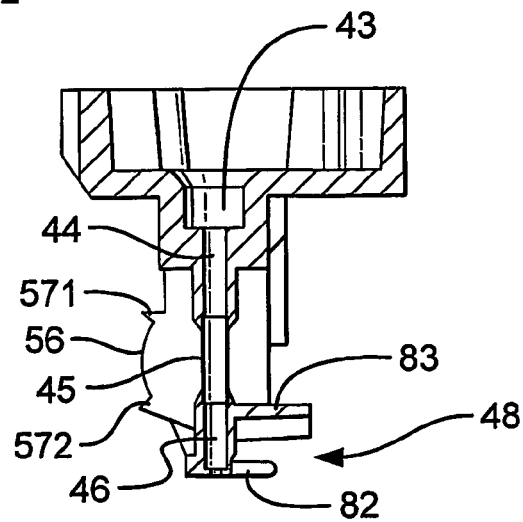

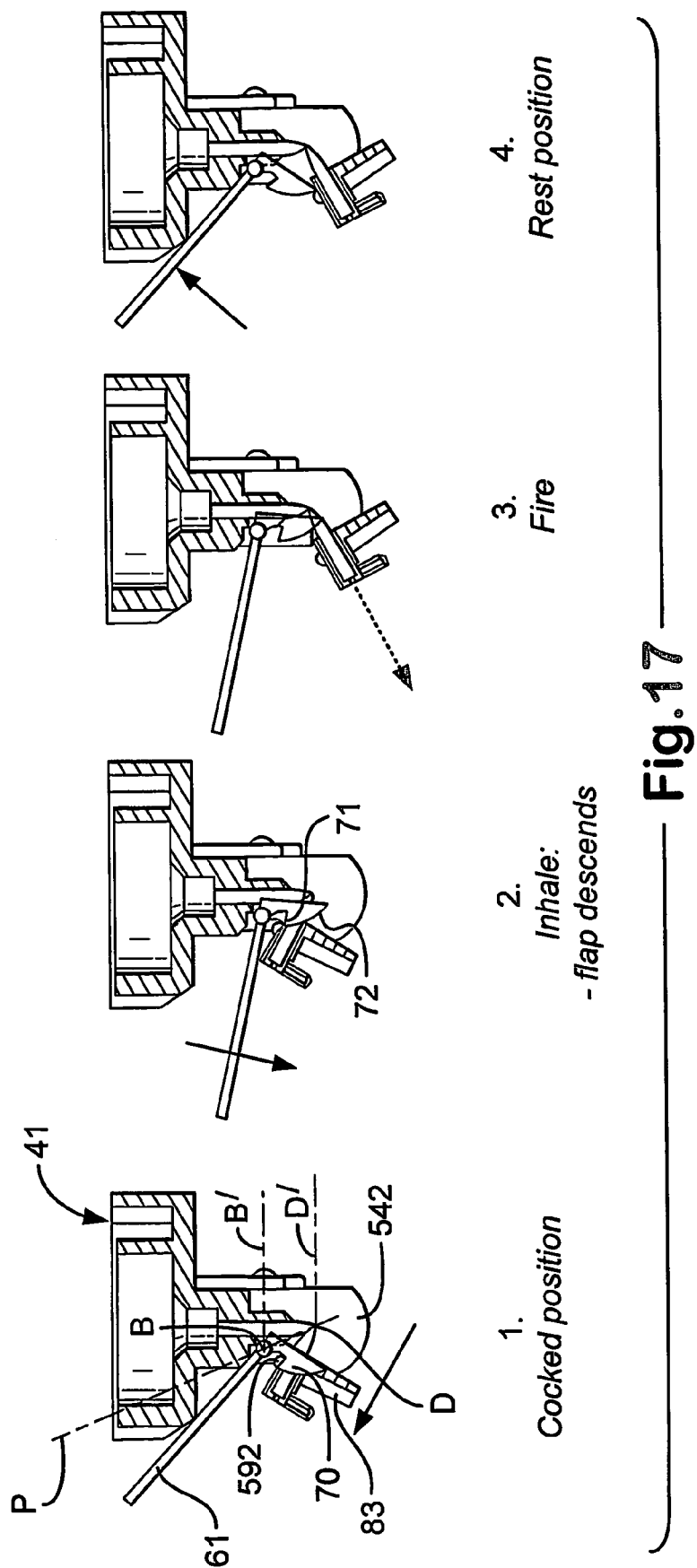

US 7,721,731 B2

DISPENSER

CROSS REFERENCE TO RELATED APPLICATIONS

This application is for entry into the U.S. national phase under §371 for International Application No. PCT/GB04/000706 having an international filing date of Feb. 20, 2004, and from which priority is claimed under all applicable sections of Title 35 of the United States Code including, but not limited to, Sections 120, 363 and 365(c), and which in turn claims priority under 35 USC §119 to U.K. Patent Application No. 0304000.3 filed on Feb. 21, 2003.

TECHNICAL FIELD

The present invention relates to a dispenser, particularly though not exclusively for dispensing aerosol or powder borne medicaments.

BACKGROUND OF THE INVENTION

In my prior International Patent Application, WO 98/41254, ("My First International Application") at least as amended on entry in the European Regional Phase, there is described and claimed:

A dispenser for a gaseous, gas borne or droplet substance, the dispenser including:
  a body having a mouthpiece with an inhalation/insufflation orifice at its end;
  a junction in the body for a source of gas or evaporable liquid comprising or containing the said substance (the source being carried by the body); and
  a breath actuable valve, for controlling the release of said gas or liquid, comprising:
    a valve inlet connected to the junction;
    a valve outlet;
    a flexible tube extending from the junction, between the inlet and the outlet, for receiving the said gas or liquid, the tube having a portion which is movable between a closed position in which the tube is kinked for closure of the valve and an open position in which the tube is un-kinked for opening of the valve; and
    a movable member, for moving the movable portion of the tube to control its kinking, and being movably mounted in the body for movement by the act of inhalation from a rest position towards the orifice—or at least in the direction of air flow through the dispenser;
  the tube being kinked to an obturating extent when the movable member is in a rest position and un-kinked when the movable member is moved on inhalation for release of the gas or liquid.

I regard My First International Application as protecting, inter alia, an inhaler with a kink valve.

I improved on the dispenser of My First International Application and in my International Patent Application No. WO 02/11802, ("My Second International Application") there is described in and claimed:

A dispenser for a gaseous, gas borne or droplet substance contained in a source thereof, the dispenser including:
  a body with a mouthpiece;
  a junction member in the body for the substance source; and
  a breath actuable valve, for controlling the release of the gas or liquid containing or comprising the substance, the valve comprising:
    a flexible tube for receiving the said gas or liquid, the tube extending from a valve inlet connected to the junction member and having a portion which is kinkable for closure of the valve and movable to an open position in which the tube is un-kinked for opening of the valve; and
    a member arranged for movement in the body by inhalation to un-kink the valve;
    the tube being kinked to an obturating extent when the movable member is in a ready position and un-kinked when the movable member is moved on inhalation for release of the gas or liquid;
wherein:
  the movable member is or includes a flap arranged in the body for action of breath on it on inhalation;
  the junction member, the flexible tube and the movable flap are a single injection moulding of plastics material; and
  the movable flap is pivotally connected to the junction member.

I regard My Second International Application as protecting, inter alia, an inhaler with a kink valve in which the kink Valve is integral with the actuation flap.

Significant features of the dispenser of My Second International Application are:

1. The junction member is slidably mounted in the body for movement in a direction for dispensing a dose of the substance from the source and the dispenser includes:
  means for pivoting the flap to its ready position on or prior to initial movement of the junction member and
  junction member resilient means for returning the junction member after release of the dose.

2. The junction member resilient means is a spring in the source and the dispenser includes:
  means for locating the source in the body with the junction member being slidable towards it and
  means for displacing the junction member towards the source for dispensing the dose into the kinked tube.

3. The means for displacing the junction member comprises:
  a grippable member rotatably arranged on the body and
  a rotary-to-linear motion conversion mechanism, arranged to convert rotary motion of the grippable member to linear motion for displacing the junction member towards the source and the means for pivoting the flap is incorporated in the motion conversion mechanism.

Additionally I made other improvements on the dispenser of My First International Application and in my International Patent Application No. WO 02/058772, ("My Third International Application") there is described in and claimed:

A dispenser including in common with that of My First International Application:
  a body with a mouthpiece;
  a junction in the body for the substance source; and
  a breath actuable valve, for controlling the release of the gas or liquid containing or comprising the substance, the valve comprising:
    a flexible tube for receiving the said gas or liquid, the tube extending from a valve inlet connected to the junction and having a portion which is kinkable for closure of the valve and movable to an open position in which the tube is un-kinked for opening of the valve; and
    an outlet member arranged for movement in the body on inhalation to un-kink the valve;

the tube being kinked to an obturating extent when the outlet movable member is in a ready position and un-kinked when the outlet movable member is moved on inhalation for release of the gas or liquid;

the dispenser also including:

a sear to hold the outlet movable member in the ready position closing of the tube by kinking prior to inhalation and a breath actuatable flap arranged in the body for movement on inhalation to release the sear and allow the outlet movable member to move for release of the gas or liquid.

I regard My Third International Application as protecting, inter alia, an inhaler with a kink valve in which the kink valve is formed separately from the actuation flap, and released by a sear on the actuation flap.

SUMMARY OF THE INVENTION

The object of the present invention is to provide further improvements in the series of inventions the subject of my three international applications, and in particular to improve the Flap arrangement of My Third International Application in an alternative to My Second International Application in which the kink valve is integral with the actuation flap.

According to the invention there is provided a dispenser for dose dispensing of a gaseous, gas borne or droplet substance from a source thereof, the dispenser comprising:

a body with a mouthpiece;

a junction member in the body and having:

a socket for receiving a spout of the substance source;

a breath actuatable valve incorporated with the junction member, for controlling the release of the gas and/or liquid containing or comprising the substance, the valve comprising:

a flexible tube for receiving a dose of the said substance gas or liquid, the tube extending from a valve inlet connected to the junction member spout and having:

a portion which is kinkable for closure of the valve and movable to a release position in which the tube is un-kinked for opening of the valve and an outlet end movable for kinking/unkinking of the tube; and an outlet member carrying the outlet end of the flexible tube and pivotally connected to the junction member for control of kinking/un-kinking movement of the flexible tube;

the tube being kinked to an obturating extent when the pivoted outlet member is in a ready position and un-kinked when the pivoted outlet member is moved its release position; and a sear on the outlet member to hold it in the ready position prior to inhalation;

a breath actuatable flap carried on the junction member and arranged for action of inhalation breath on it, the flap having:

a latch complementary to the sear and the flap being arranged:

to latch the pivoted outlet member for kinked closure of the flexible tube via action of the latch and the sear and to release the pivoted outlet member for unkinking of the tube, and substance release, on inhalation by release of the sear by the latch and movement to its release position of the outlet member.

Normally, the source will be a pressurised, medicament container with a metered dose valve held in the body and the junction member is slidably mounted in the body for movement towards the container and dispensing of a dose to the valve via the junction member.

In the preferred embodiment, the dispenser includes a pivotally mounted closure for the mouthpiece, the closure having a pivot shaft and a cam arranged on the shaft for moving the junction member towards the source for dose release.

In such a dispenser, an expedient feature is provision of a finger on the flap and a finger fast with the pivotal closure are arranged to co-operated for release the pivoted outlet member from its cocked position in the event of closure of the device, without inhalation.

Preferably, pivoted outlet member is arranged to move under pressure in the kink tube and/or under resilience, particularly of the kink tube.

Normally, the junction member, the kink tube and the pivoted outlet member are an integral plastics material injection moulding, the pivoted outlet member being pivoted to the junction member by one or more living hinges and having an outlet nozzle downstream of the kink tube.

Conveniently, the junction member has two pairs of pivot clips for pivotally carrying the flap, which has two moulded pivot pins at its proximal edge.

Again in the preferred embodiment, the flap has at least one latch for co-operating with the or each sear on the pivoted outlet member, the arrangement being such that the latches and the sears when engaged are positioned between parallel planes passing through the pivot axes of the flap and the outlet member on the junction member, whereby breath movement of the flap moves the latches towards the common plane to release the sears and the outlet member. The latches and the sears when engaged are positioned to one side of a common plane passing through the pivot axes. The latches have cam surfaces opposite latch surfaces, for the sears to act on during cocking of the dispenser.

Preferably, the flap has an integral spring acting on the junction member to bias it normally to an inhalation-flow-upstream position; and the flap includes a finger arranged to act on the pivoted outlet member to urge it towards its open position as the flap moves under the action of inhalation breath.

BRIEF DESCRIPTION OF THE DRAWINGS

To help understanding of the invention, a specific embodiment thereof will now be described by way of example and with reference to the accompanying drawings, in which:

FIG. 4 is an exploded view of the dispenser;

FIG. 9 is an oblique view from the front and below of a junction member of the dispenser, in its as moulded configuration;

FIG. 10 a rear view of the junction member;

FIG. 11 is a cross-sectional side view of the junction member on the line A-A in FIG. 10;

FIG. 17 is a series of scrap views of the flap and kink valve in the junction member illustrating operation of the valve.

DETAILED DESCRIPTION

Figure 1:
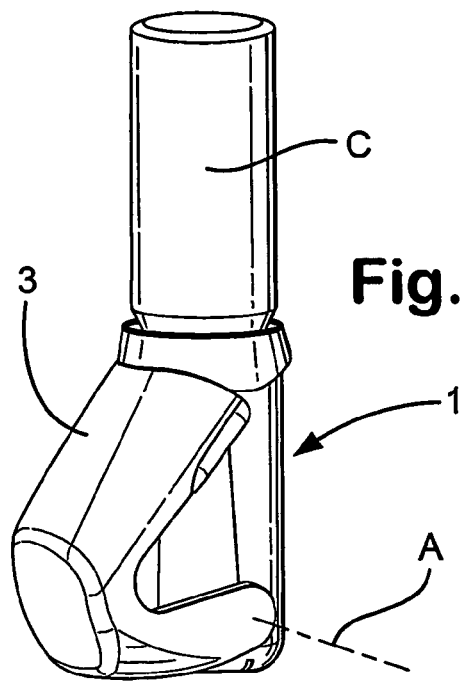
FIG. 1 is a perspective view of a dispenser according to the invention in closed position.

Referring first to FIGS. 1 to 4 of the drawings, the dispenser thereshown is a development of that shown in FIGS. 13 to 17 of My Second International Application, although it includes features of My Third International Application The dispenser has a body 1 with a mouthpiece 2 and a pivoted mouthpiece cover 3. The mouthpiece is formed as an aperture 4 in a separate body part 5 clipped to a main body part 6. The main part 6 has upper and lower formations 7,8 and the mouthpiece part has upper and lower complementary formations 9,10 which engage when the mouthpiece part is slid from below to engage with the main part. The separate body part 5 is cutaway 11 with respect to the main body part 6, to define an air inlet 12 exposed by the cover 3 when this is open. A medicament can C is fitted to the body part 6. Immediately within the air inlet 12 is a guard 13 against little fingers. It is backed up by strengthening flanges 14, which additionally guard the cam mechanism to be described in the next paragraph.

Above the guard 13, a series of four ribs extend and provide further guarding. The end ones 151 are longer and provide eventual stops for the flap of the actuation mechanism described below in the case of malfunction. The inner ones 152 act as flow restrictors to cause a pressure drop between the inlet 12 and the aperture 4 when the mechanism has been actuated, primarily to control the air flow rate through the device.

Figure 6:
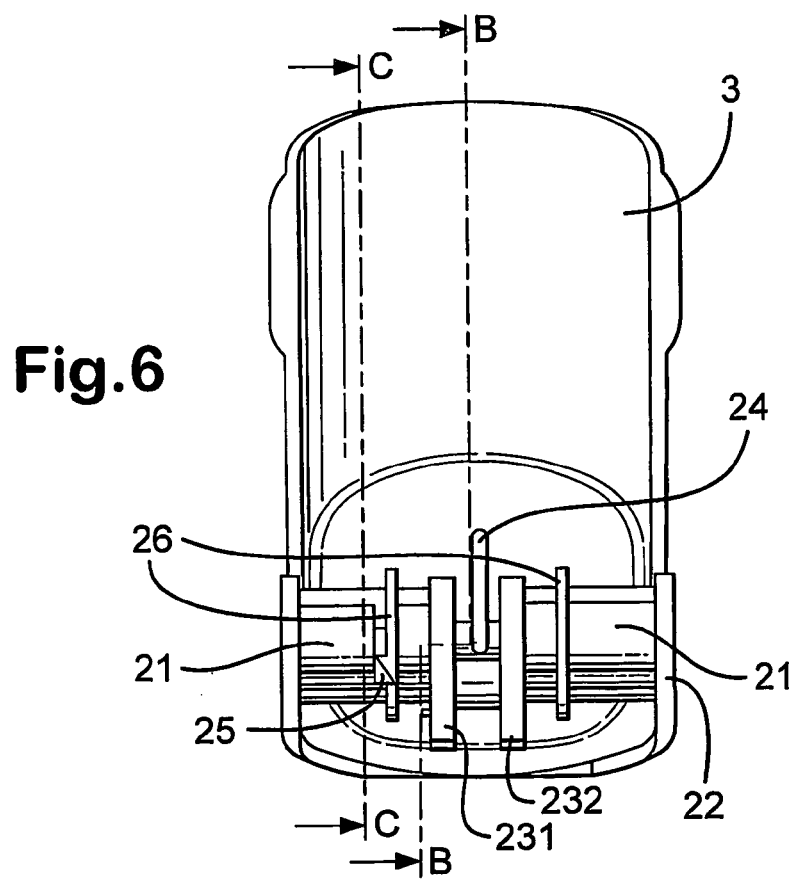
FIG. 6 is an inside, rear, view of a cover of the dispenser.
Figure 7:
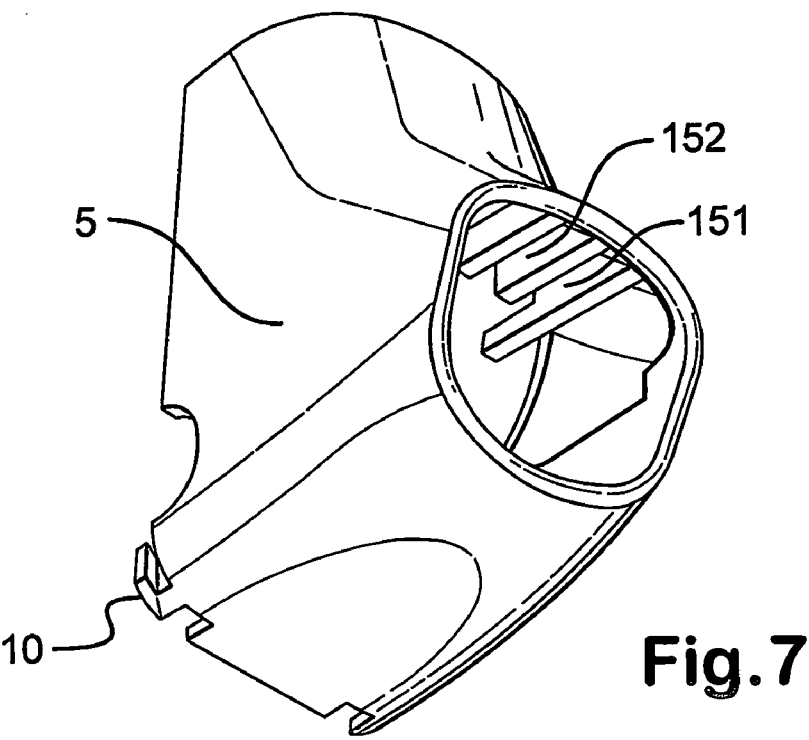
FIG. 7 is an oblique view from the front and below of a front body part of the dispenser.
Figure 8:
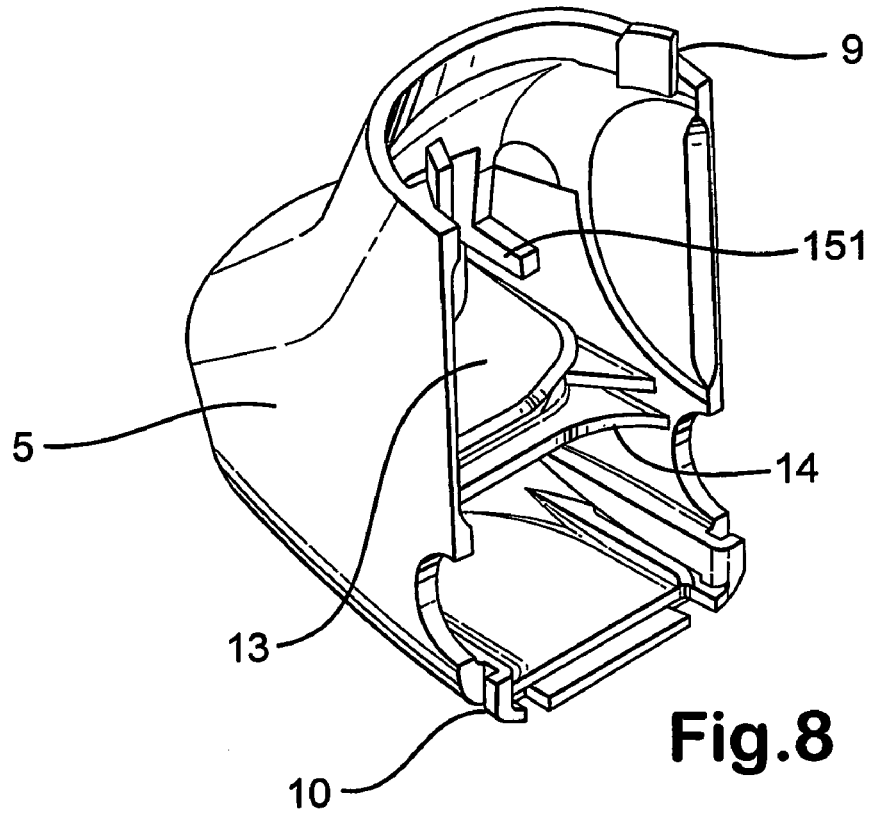
FIG. 8 is a view from the opposite direction of the front body part.
Figure 12:
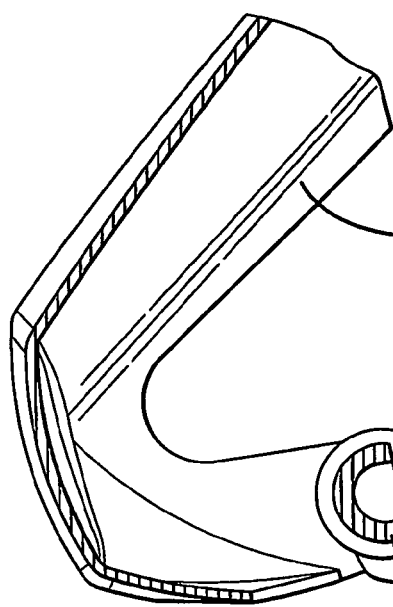
FIG. 12 is a cross-sectional side view of the cover on line C-C in FIG. 6.
Figure 13:
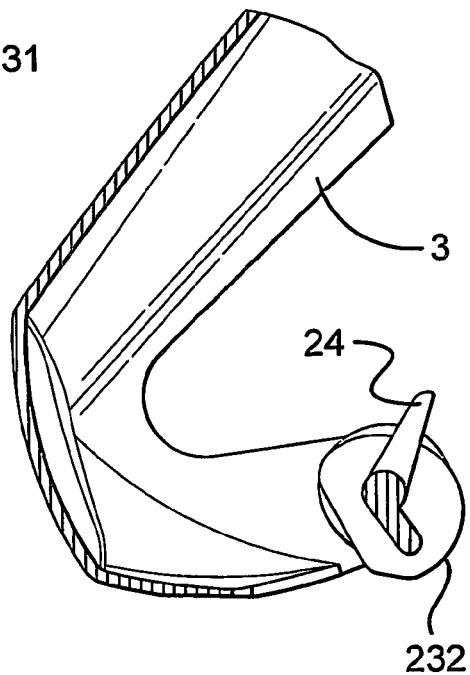
FIG. 13 is a central, cross-sectional side view of the cover on line B-B in FIG. 6.

The cover 3—see FIGS. 6,12 & 13—is pivoted about an axis A low in the body at the joint between the two body parts. Integrally moulded with the cover 3 is a C section shaft 21, via webs 22. The shaft carries a cam arrangement 23, comprising two cam lobes 231 and 232, together with two fingers, a central one 24 and a outer one 25. The latter is integral with one of a pair of discs 26, between which and the cam lobes, the shaft is bearingly supported by part circular journals 27 in flanges 28 integrally moulded within the main body part 6. At the joint line between the two body 5,6 further coaxial scallops 29 are provided for the shaft 21.

The body parts 5,6, and the cover 3 (with the shaft and cam arrangement) are of moulded polypropylene material, whereby they can be fitted together with a modicum of flexure.

The can C is held in an opening 31 at the upper end of the main body part 6, where the body part extends completely around a valve crimp portion CP of the can C. The actual arrangement for holding the can connected to the body part forms no part of this invention, but can be as disclosed in my recently filed British Patent application No 0227489.2.

Moulded inside the main body part, inwards of the opening are internal grooves 32. A junction member 41—see FIGS. 9,10 & 11—is slidably accommodated in the body with the grooves 32 engaged by ribs 42 in its periphery. The junction member also is of moulded polypropylene. Centrally, the junction member has a socket 43 for an outlet stem S of the can. The socket is continued by a passage 44, which has a thin wall, kinkable portion 45 and a nozzle end 46. This is in a movable valve part 48 of the junction member. The main part 411 of the junction member 41 and the valve part 48 are connected by a living hinge 49, in the form of two membranes 491,492 at respective sides of the junction member between lugs 501,502 and tabs 511,512. The tabs are interconnected by a bar 52 having the nozzle aperture 53. Between the lugs 501,502 and on either side of the kink tube 45 extend two followers 541,542, which are integral with the respective lugs 501,502 and are acted on by the cam lobes 231,232, with the interposition of tongues 551,552 extending from the inside of the main body part 6 to react lateral action on the junction member from the cam. The followers 541,542 have radiused portions 56, centred on the hinge axis, with upper and lower valve travel stops 571,572.

Additionally, the lugs 501,502 carry on their sides facing the same direction as the radiused portions 56, pairs of pivot clips 581,582 for pivotally locating the flap to be described below. One the same side of moulding a pair of sears 591,592 are provided on the tabs 511,512.

Figure 14:
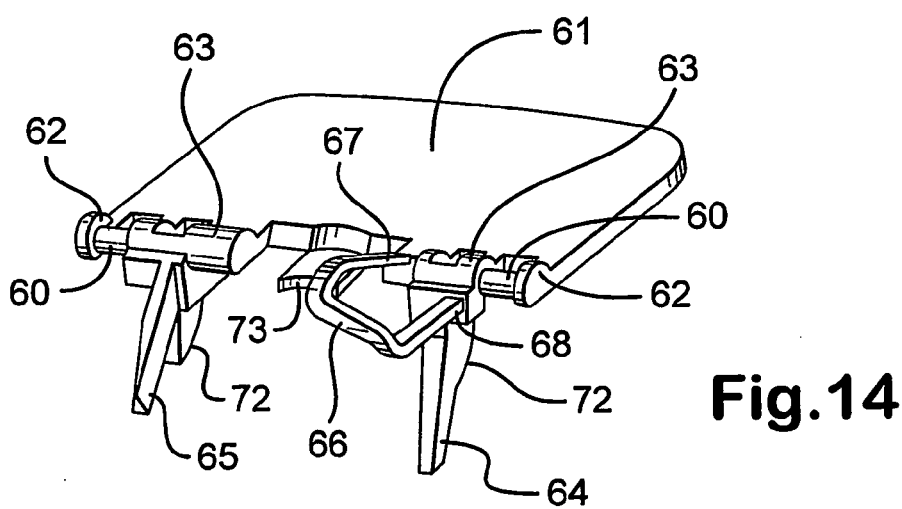
FIG. 14 is a perspective view from behind of a flap of the dispenser.
Figure 15:
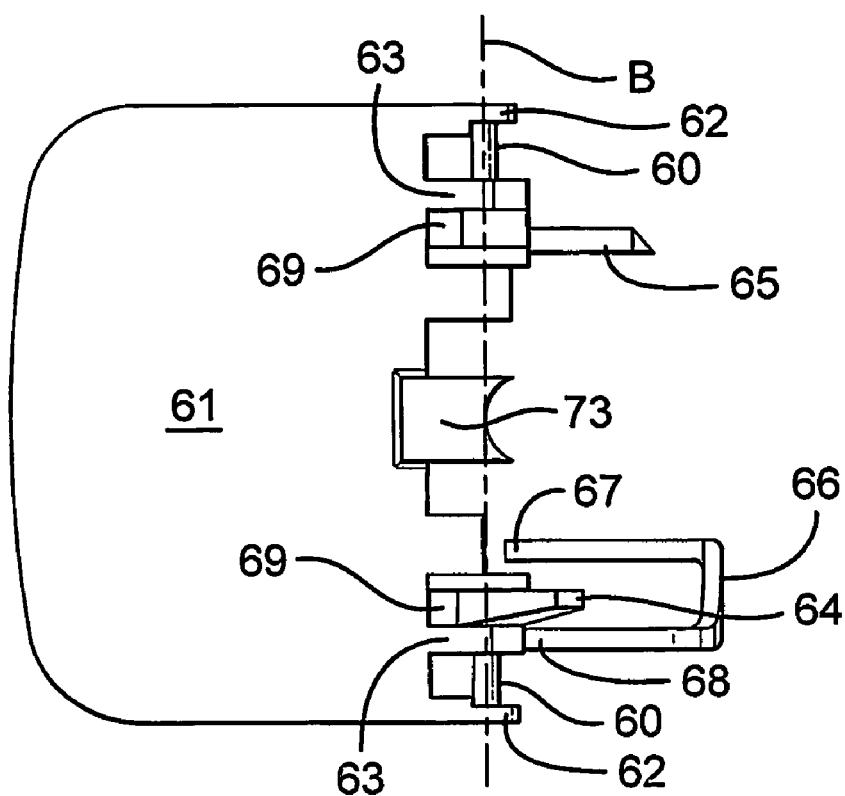
FIG. 15 is a plan view of the flap.
Figure 16:
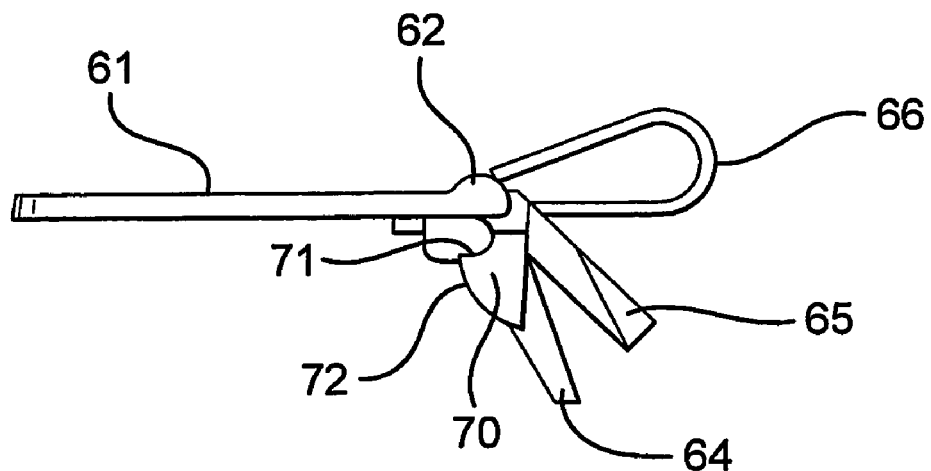
FIG. 16 is a side view of the flap.

The flap 61—see FIGS. 14,15 & 16—has a pivot axis B. At opposite ends of the axis, the flap has small thrust flanges 62, with pivot pins 60 set in from them. Inboard of the pins, two swellings 63 are formed. Each has a finger 64,65 extending obliquely down from it. One of the swellings has a spring loop 66 extending backwards, inwards and forwards again with its distal end 67 adjacent the swelling to which its proximal end 68 is attached. Set into the swellings from the pins are apertures 69 formed from above and latches 70 extending below the apertures. These have latch surfaces 71 formed during moulding by projections through the apertures. The latches have cam surfaces 72. These are positioned so as to abut the sears 591,592 as the device is cocked. The sears then pass over the end of the cam surfaces and come to engage on the latch surfaces. The final feature of flap is a tongue 73, which extends between the followers 541,542 to control air leakage as might otherwise occur.

The operation of the device will now be described.

Figure 3:
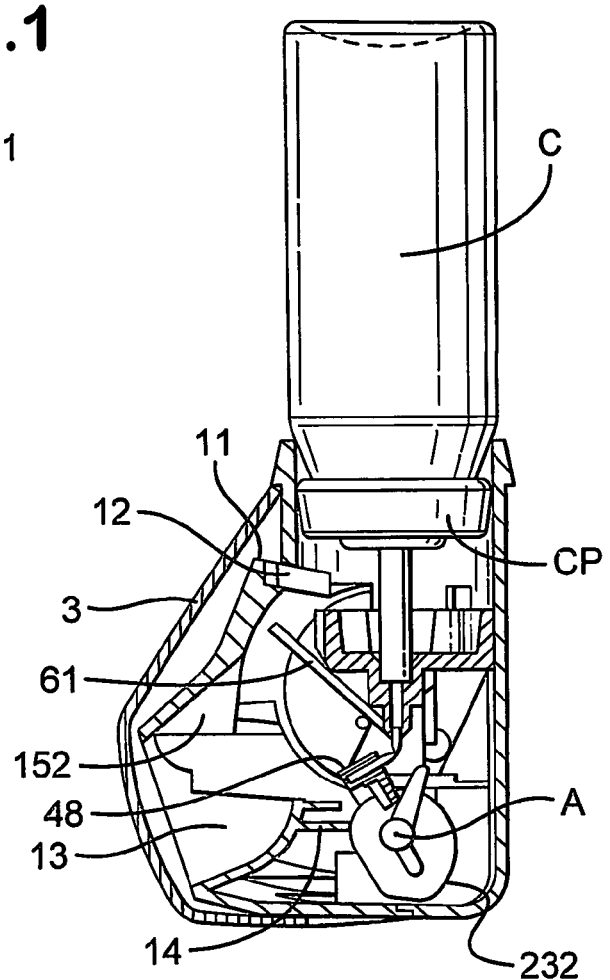
FIG. 3 is a central cross-sectional view of the dispenser closed.
Figure 2:
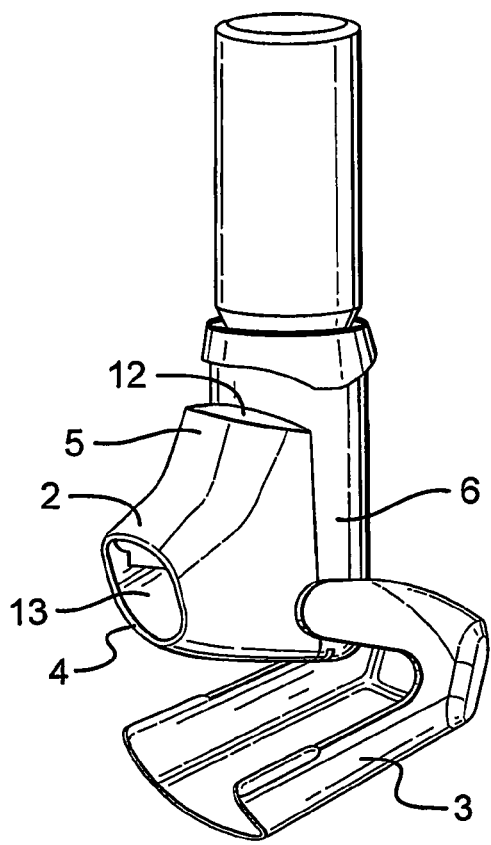
FIG. 2 is a similar view of the dispenser in open position.
Figure 5:
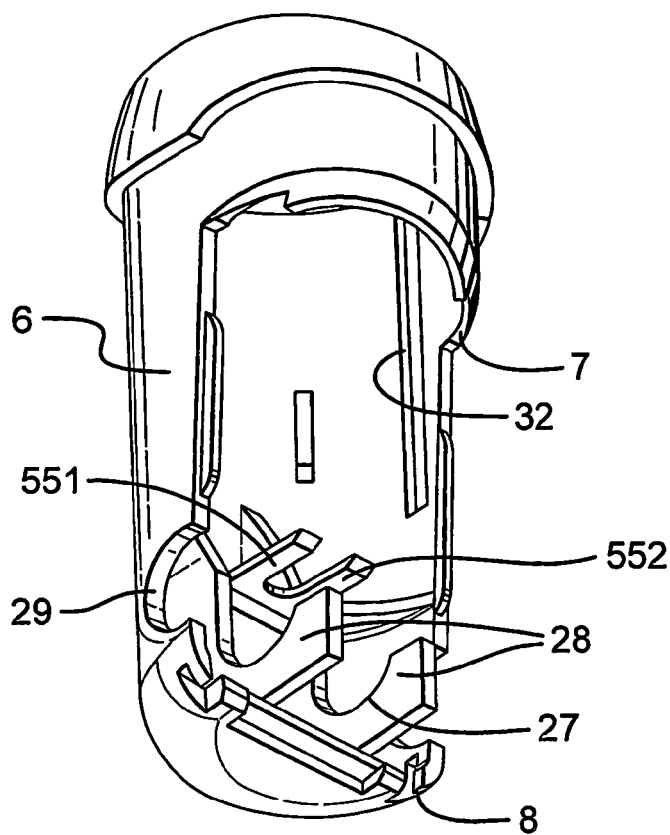
FIG. 5 is an inside, front, rear view of a main body part of the dispenser.

Initially, the device is closed and the flexible members are relaxed. In others words the flap is in its upper, upstream position, as shown in FIGS. 3 & 17 (1), and the hingeable part 48 of the junction member is in its lower position. The flap is held in this position by its spring 66, bearing with it distal end 67 on an abutment 81 set in from the lug 502. The movable portion of the junction member is pivoted down, due to the tendency of the kink tube to straighten to its as moulded state. Its position is controlled by two fingers 82 projecting laterally from the bar 52 to abut with the cam lobes 231,232.

On opening of the cover, the cam lobes act via the tongues 551,552 on the followers 541,542. They lift the junction member 41 against the internal spring—not shown—of metering valve in the can, with displacement of stem S inwards of the can. As the cover is rotated, the central finger 24 between the cam lobes engages with a notched projection 83 between the fingers 82 on the hingeable part of the junction member. This action lifts the movable member and closes the kink tube. Further lifting opens the can's valve and a dose metered by the can's valve is released into the upper part of the tube. It is retained there by the kink tube acting as a closed valve.

Naturally, the dose is retained only whilst the hingeable part 48 of the valve is retained in the upper positioned to which it has been moved. This is achieved by the sears 591, 592 running along the cam surfaces 72 and engaging with the latch surfaces 71. As the sears move into engagement, the latches 70 are moved back, rotating the flap down somewhat against the action of the spring 66. Once the sears clear the end of the cam surfaces, the spring moves the latches in under the sears. There is clearance for the hingeable part 48 to continue to pivot further, until the central finger 24 passes on out of engagement with the projection 83. The device is now cocked for inhalation.

Breathing in through the mouthpiece causes an air flow down through the air inlet 12, exposed on opening of the cover, and impinging on the flap 61 as such. It is blown down against the action of the spring 66, releasing the sears. The kink tube tends to straighten under the action of its own resilience and the pressure of the retained dose; and the dose is released through the nozzle into the mouthpiece for inhalation, the nozzle traversing the mouthpiece aperture 4 as the dose is released.

The geometrical arrangement of the flap and the hingeable part 48 can be seen in FIG. 17. The pivot axis B of the flap is spaced from the pivot axis D of the hingeable part, with the point of engagement of the sears 591 and latches 70 lying between parallel planes B' and D' passing through the axes B and D. The actual points of engagement lie to the flap side of a common plane P passing through the axes.

After use, the cover is closed. The cams allow the movable member to return down and the finger 24 passes the notched projection 83 as a result of cam surfaces 84 on their reverse faces.

Should the kink tube have lost its resilience and be slow in opening, the finger 64, at the spring side of the flap pivot acts on a lug 85 moulded integrally with the hingeable part's lug 511 and extending back past the hinge axis H. This the hingeable part is moved to its open position.

A further eventuality is closure of the cover without inhalation. In this event, the finger 65 is engaged by the finger 25 to deflect the flap to its position in which the hingeable part releases the dose. The spring 66 returns the flap after this movement of it (which of course occurs on closure even if the dose has been released by inhalation). Thus the device is returned to its initial position in which the plastics material resilient features are relaxed.

All the components are of device (excluding the can) are moulded of polypropylene, with the exception of the flap, whose spring dictates use of acetal.

The invention claimed is:

1. A dispenser for dose dispensing of a gaseous, gas borne or droplet substance from a source thereof, the dispenser comprising:
    a body with a mouthpiece;
    a junction member in the body and having:
        a socket for receiving a spout of the substance source;
    a breath actuatable valve incorporated with the junction member, for controlling the release of the gas and/or liquid containing or comprising the substance, the valve comprising:
        a flexible tube for receiving a dose of the said substance gas or liquid, the tube extending from a valve inlet connected to the junction member spout and having:
            a portion which is kinkable for closure of the valve and movable to a release position in which the tube is un-kinked for opening of the valve and
            an outlet end movable for kinking/unkinking of the tube; and
        an outlet member carrying the outlet end of the flexible tube and pivotally connected to the junction member for control of kinking/un-kinking movement of the flexible tube;
            the tube being kinked to an obturating extent when the pivoted outlet member is in a ready position and un-kinked when the pivoted outlet member is moved its release position; and
        a sear on the outlet member to hold it in the ready position prior to inhalation;
    a breath actuatable flap carried on the junction member and arranged for action of inhalation breath on it, the flap having:
        a latch complementary to the sear and
        the flap being arranged:
            to latch the pivoted outlet member for kinked closure of the flexible tube via action of the latch and the sear and
            to release the pivoted outlet member for unkinking of the tube, and substance release, on inhalation by release of the sear by the latch and movement to its release position of the outlet member,
    characterised in that the source is a pressurised, medicament container with a metered dose valve held in the body and
    in that the junction member is slidably mounted in the body for movement towards the container and
    in that dispensing of a dose to the valve via the junction member.

2. A dispenser as claimed in claim 1, including a pivotally mounted closure for the mouthpiece, the closure having a pivot shaft and a cam arranged on the shaft for moving the junction member towards the source for dose release.

3. A dispenser as claimed in claim 2, wherein a finger on the flap and a finger fast with the pivotal closure are arranged to co-operated for release the pivoted outlet member from its cocked position in the event of closure of the device, without inhalation.

4. A dispenser as claimed in claim 3, wherein the pivoted outlet member is arranged to move under pressure in the kink tube and/or under resilience, particularly of the kink tube.

5. A dispenser as claimed in claim 4, wherein the junction member, the kink tube and the pivoted outlet member are an integral plastics material injection moulding, the pivoted outlet member being pivoted to the junction member by one or more living hinges and having an outlet nozzle downstream of the kink tube.

6. A dispenser as claimed in claim 5, wherein the junction member has two pairs of pivot clips for pivotally carrying the flap, which has two moulded pivot pins at its proximal edge.

7. A dispenser as claimed in claim 6, wherein the flap has at least one latch for co-operating with the or each sear on the pivoted outlet member, the arrangement being such that the latches and the sears when engaged are positioned between parallel planes passing through the pivot axes of the flap and the outlet member on the junction member, whereby breath movement of the flap moves the latches towards the common plane to release the sears and the outlet member.

8. A dispenser as claimed in claim 7, wherein the latches and the sears when engaged are positioned to one side of a common plane passing through the pivot axes.

9. A dispenser as claimed in claim 8, wherein the latches have cam surfaces opposite latch surfaces, for the sears to act on during cocking of the dispenser.

10. A dispenser as claimed in claim 9, wherein the flap has an integral spring acting on the junction member to bias it normally to an inhalation-flow-upstream position.

11. A dispenser as claimed in claim 10, wherein the flap includes a finger arranged to act on the pivoted outlet member to urge it towards its open position as the flap moves under the action of inhalation breath.

12. A dispenser as claimed in claim 1, wherein the pivoted outlet member is arranged to move under pressure in the kink tube and/or under resilience, particularly of the kink tube.

13. A dispenser as claimed in claim 1, wherein the junction member, the kink tube and the pivoted outlet member are an integral plastics material injection moulding, the pivoted outlet member being pivoted to the junction member by one or more living hinges and having an outlet nozzle downstream of the kink tube.

14. A dispenser as claimed in claim 5, wherein the flap has at least one latch for co-operating with the or each sear on the pivoted outlet member, the arrangement being such that the latches and the sears when engaged are positioned between parallel planes passing through the pivot axes of the flap and the outlet member on the junction member, whereby breath movement of the flap moves the latches towards the common plane to release the sears and the outlet member.

15. A dispenser as claimed in claim 14, wherein the latches and the sears when engaged are positioned to one side of a common plane passing through the pivot axes.

16. A dispenser as claimed in claim 7, wherein the latches have cam surfaces opposite latch surfaces, for the sears to act on during cocking of the dispenser.

17. A dispenser as claimed in claim 1, wherein the flap has an integral spring acting on the junction member to bias it normally to an inhalation-flow-upstream position.

18. A dispenser as claimed in claim 1, wherein the flap includes a finger arranged to act on the pivoted outlet member to urge it towards its open position as the flap moves under the action of inhalation breath.

* * * * *